United States Patent [19]

Maravetz

[11] Patent Number: 5,321,002
[45] Date of Patent: Jun. 14, 1994

[54] HERBICIDAL DERIVATIVES OF 2-(1-ARYL-4-CYANO-5-PYRAZOLYLME-THYLENEIMINOOXY)ALKANOIC ACIDS

[75] Inventor: Lester L. Maravetz, Westfield, N.J.

[73] Assignee: FMC Corporation, Philadelphia, Pa.

[21] Appl. No.: 105,233

[22] Filed: Aug. 11, 1993

[51] Int. Cl.$^5$ .................. A01N 43/56; C07D 401/04
[52] U.S. Cl. .................. 504/253; 504/280; 504/270; 546/279; 548/375.1; 548/365.7; 548/228; 548/229
[58] Field of Search ............. 504/253, 280, 270; 546/279; 548/375.1, 365.7, 228, 229

[56] References Cited

U.S. PATENT DOCUMENTS 5,198,014  3/1993  Maravetz ..................... 504/225
5,250,504  10/1993  Maravetz ..................... 504/280

FOREIGN PATENT DOCUMENTS 234045  9/1987  European Pat. Off. .

*Primary Examiner*—Jane T. Fan
*Attorney, Agent, or Firm*—H. Robinson Ertelt; Robert M. Kennedy

[57] ABSTRACT

Herbicidal compounds, compositions containing them, and a method for controlling weeds by application of the compositions are disclosed. The herbicidal compounds are 2-(1-aryl-4-cyano-5-pyrazolylmethyleneiminooxy)alkanoic acid derivatives of the structure:

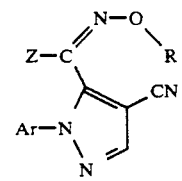

in which R is lower alkyl, lower alkenyl, or lower alkynyl, each optionally substituted with halogen, or $CH(R^1)-C(O)-Y-R^2$; $R^1$ is hydrogen or lower alkyl; $R^2$ is one of a variety of substituents; Y is O or NH; Z is lower alkyl or lower alkoxy; and Ar is 3-chloro-5-trifluoromethyl-2-pyridyl, 2,6-dichloro-4-trifluoromethylphenyl, or 2,4,6-trichlorophenyl.

14 Claims, No Drawings

HERBICIDAL DERIVATIVES OF 2-(1-ARYL-4-CYANO-5-PYRAZOLYLMETHYLENEIMINOOXY)ALKANOIC ACIDS

This invention pertains to novel herbicidal derivatives of 2-(1-aryl-4-cyano-5-pyrazolylmethyleneiminooxy)alkanoic acids and their use for weed control in agriculture, horticulture, and other fields where it is desired to control unwanted plant growth. The use of this class of compounds as herbicides has not previously been reported.

A number of previously reported herbicidal 1-arylpyrazoles are described in U.S. Pat. No. 5,198,014, which differs from the compounds here disclosed in having an acrylic acid residue in the 5-position instead of a methyleneiminooxyalkanoic acid residue.

Many derivatives of oximes of pyrazolecarboxaldehyde have been reported as cephalosporins or intermediates in the preparation of cephalosporins. In these compounds the pyrazole ring is unsubstituted except in what corresponds to the 5-position of the compounds of the invention. There is no suggestion that any of these compounds might have herbicidal activity.

No reference has been found disclosing the compounds of the invention for any purpose. The class of compounds most closely related to the present compounds is found in European Patent Application EP-234-045A, which claims insecticidal, acaricidal, and fungicidal activity for compounds of the following formula:

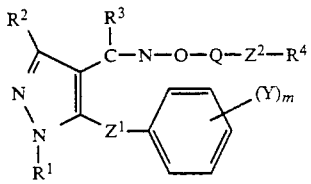

wherein
$R^1$ is $C_{1-4}$ alkyl or phenyl;
$R^2$ is H, $C_{1-5}$ alkyl, $C_{1-3}$ haloalkyl, or phenyl;
$R^3$ is H, $C_{1-4}$ alkyl, or phenyl;
$R^4$ is H, $C_{2-4}$ alkylcarbonyl, benzoyl, naphthyl, substituted phenyl, 5-substituted 2-oxazolidinone;
$Z^1$ is O or S;
$Z^2$ is O, S, or a single bond;
Q is a $C_{1-8}$ alkylene, optionally substituted with halogen or phenyl, $C_{3-12}$ alkenylene, or $C_{3-6}$ alkynylene; and
m is 1, 2, or 3.

As will be apparent, the substitution pattern of these prior art compounds differs substantially from that of the compounds of the invention.

It has now been discovered that 2-(1-aryl-4-cyano-5-pyrazolylmethyleneiminooxy)alkanoic acid derivatives of the following structure are active as herbicides:

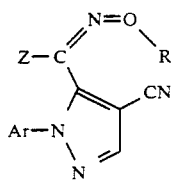

wherein

R is lower alkyl, lower alkenyl, or lower alkynyl, each optionally substituted with halogen, or $CH(R^1)$—$C(O)$—Y—$R^2$;
$R^1$ is hydrogen or lower alkyl;
$R^2$ is hydrogen, lower alkyl, lower alkenyl, lower alkynyl, lower haloalkyl, lower cyanoalkyl, phenyl, oxazolyl, isopropylideneimino, methylthiomethyl, furanylmethyl, tetrahydrofuranylmethyl, ammonium substituted with 1 to 3 lower alkyl, optionally substituted with halo or hydroxy, benzyl, optionally substituted with 1 to 3 halo or lower alkyl, and when Y is NH may be lower alkylsulfonyl or benzylsulfonyl;
Y is O or NH;
Z is hydrogen or lower alkoxy; and
Ar is 3-chloro-5-trifluoromethyl-2-pyridyl, 2-6-dichloro-4-trifluoromethylphenyl, or 2,4,6-trichlorophenyl.

"Lower" refers to groups having no more than six carbon atoms, preferably no more than four.

Preferred compounds are those in which
R is $CH(R^1)$—CO—Y—$R^2$;
$R^1$ is hydrogen or lower alkyl;
$R^2$, when Y is O, is hydrogen, lower alkyl, lower haloalkyl, lower cyanoalkyl, or benzyl, optionally substituted with 1-3 halo, and when Y is NH is lower alkyl, lower alkylsulfonyl, or benzylsulfonyl;
Z is hydrogen;
Ar is 3-chloro-5-trifluoromethyl-2-pyridyl or 2,6-dichloro-4-trifluoromethylphenyl; and
halo is chlorine or fluorine.

Particularly preferred compounds are those in which
R is $CH(R^1)$—CO—Y—$R^2$;
$R^1$ is lower alkyl;
$R^2$, when Y is O, is lower alkyl, lower haloalkyl, or benzyl, optionally substituted with 1-3 halo, and when Y is NH is lower alkylsulfonyl;
Z is hydrogen;
Ar is 3-chloro-5-trifluoromethyl-2-pyridyl or 2,6-dichloro-4-trifluoromethylphenyl; and
halo is chlorine or fluorine.

The compounds of the present invention were prepared by methods known to one of ordinary skill in the art.

An arylhydrazine, e.g., 3-chloro-5-trifluoromethyl-2-pyridylhydrazine, 2,6-dichloro-4-trifluoromethylphenylhydrazine, or 2,4,6-trichlorophenylhydrazine, was reacted with either ethyl 2-ethoxymethyleneacetoacetate or ethyl 2-dimethylaminomethyleneacetoacetate to produce the corresponding 1-aryl-4-ethoxycarbonyl-1H-5-methylpyrazole. Hydrolysis of the ester group to the acid was followed by reaction of the acid group with thionyl chloride and sulfamide in sulfolane, producing the corresponding 4-cyanopyrazole. Monobromination of the 5-methyl group with N-bromosuccinimide was followed by reaction of the bromomethylpyrazole with pyridine to produce the corresponding N-pyrazolylmethylpyridinium bromide. The pyridinium bromide was then reacted with N,N-dimethyl-4-nitrosoaniline to form the corresponding 5-(4-dimethylaminophenyl-N-oxyiminomethyl)pyrazole. Hydrolysis of this latter intermediate with 6N hydrochloric acid yielded the corresponding 1-aryl-4-cyano-1H-5-formylpyrazole (1), an intermediate also used in the alternative synthesis described below. Reaction of this final intermediate with 2-aminooxypropionic acid yielded the 2-[(1-aryl-4-cyano-1H-5-pyrazolyl)methyliminooxy]propionic acid. Examples 1, 3, and 6 detail this synthetic route for different aryl groups. Ester derivatives were made by reacting the propionic acid compound with methanol, for example, in the presence of p-toluenesulfonic acid (Example 2 and Example 6, Step I) or with 3-chlorophenylmethyl bromide in the presence of potassium carbonate in toluene (Example 4).

An alternative synthesis route was required to prepare Compounds 65–69. This route started with the 4-cyanopyrazole intermediate (I) described above, which was oxidized with potassium permanganate and disodium hydrogen phosphate heptahydrate in acetone to provide the corresponding 1-aryl-4-cyano-1H-5-pyrazolycarboxylic acid. Preparation of the acid chloride of this carboxylic acid was followed by the reaction of this intermediate with methyl aminoacetate and triethylamine in a cooled diethyl ether solution, yielding the corresponding N-methoxycarbonylmethoxy-1-aryl-4-cyano-1H-5-pyrazolylcarboxamide. This latter intermediate was reacted with methyl p-toluenesulfonate and potassium carbonate in N,N-dimethylformamide, yielding the desired methyl 2-[(1-aryl-4-cyano-1H-5-pyrazolyl](methoxy-methyl)iminooxy]acetate. Example 5 details this synthesis route, which is an adaptation of the process described in U.S. Pat. No. 4,931,088.

EXAMPLE 1

Synthesis of 2-[[1-(3-chloro-5-trifluoromethyl-2-pyridyl)-4-cyano-1H-5-pyrazolyl]methyliminooxy]propionic Acid (Compound 1)

Step A Synthesis of 3-chloro-5-trifluoromethylpyrid-2-ylhydrazine

To a solution of 60 mL of hydrazine monohydrate in 380 mL of ethanol was added 81 g (0.38 mole) of 2,3-dichloro-5-trifluoromethylpyridine during a period of 25 minutes. At the end of the addition the temperature had risen to 37° C. This mixture was heated to reflux and maintained at reflux for approximately 15 hours. The solvent was evaporated under reduced pressure, leaving a wet slurry that was immediately recrystallized from boiling ethanol/water (5:2). The mixture was cooled to 20° C. and then filtered. The filter cake was air-dried, yielding approximately 60 g of 3-chloro-5-trifluoromethylpyrid-2-ylhydrazine. The NMR spectrum was consistent with the assigned structure. This reaction was repeated to obtain additional material for subsequent reactions.

Step B Synthesis of ethyl 2-ethoxymethyleneacetoacetate

A mixture of 130 g (1 mole) of ethyl acetoacetate and 148.2 g (1 mole) of triethyl orthoformate in 188 mL (2 moles) of acetic anhydride was heated at reflux for 100 minutes, after which the heating was stopped, and the reaction mixture was stirred for approximately seventeen hours. After the lower boiling materials were distilled off, the following fractions were obtained from a vacuum distillation:

| Fraction | Boiling Range °C. | Distillation Pressure | Weight |
|---|---|---|---|
| 1 | 64–106 | 4.1–4.6 mm | 19.00 g |
| 2 | 106–116 | 4.5–6.0 mm | 21.01 g |
| 3 | 116–120 | 5.5–6.7 mm | 51.30 g |
| 4 | 120–122 | 6.3–6.7 mm | 26.38 g |
| 5 | 122–125 | 6.3–6.8 mm | 18.20 g |

All fractions were analyzed by NMR spectroscopy. Fractions 1–3 were combined as containing the desired product, but they also contained significant amounts of impurities. Fractions 4 and 5 were combined and were shown to contain the desired ethyl 2-ethoxymethyleneacetoacetate.

Step C Synthesis of 1-(3-chloro-5-trifluoromethyl-2-pyridyl)-4-ethoxycarbonyl-1H-5-methylpyrazole To a solution of 30 g (0.14 mole) of 3-chloro-5-trifluoromethylpyrid-2-ylhydrazine in 500 mL of ethanol was added 26.4 g (0.142 mole) of ethyl 2-ethoxymethyleneacetoacetate (combined Fractions 1–3 from Step B) in one portion. The resulting mixture was heated at reflux. After 1.5 hours about 5 g (0.03 mole) of ethyl 2-ethoxymethyleneacetoacetate was added. A second addition of approximately 1.5 g (0.0081 mole) of ethyl 2-ethoxymethyleneacetoacetate was made 1.25 hours later. After heating for an additional period, the reaction mixture was cooled, and the solvent was evaporated under reduced pressure, leaving a red oil weighing 48 g as a residue. This oil was dissolved in 225 mL of methylene chloride, and the resulting solution was washed successively with 10% hydrochloric acid, a saturated aqueous solution of sodium bicarbonate, and water. The solution was dried over anhydrous magnesium sulfate, filtered, and the solvent evaporated under reduced pressure, leaving 35.4 g of 1-(3-chloro-5-trifluoromethyl-2-pyridyl)-4-ethoxycarbonyl-1H-5-methylpyrazole as a red oil. The NMR spectrum of this oil was consistent with the structure of the desired product, but it also showed that there were significant amounts of contaminants present. This product was used in the next step without further purification.

Step D Synthesis of 1-(3-chloro-5-trifluoromethyl-2-pyridyl)-4-carboxy-1H-5-methylpyrazole A mixture of 34.5 g (approximately 0.1 mole) of impure 1-(3-chloro-5-trifluoromethyl-2-pyridyl)-4-ethoxycarbonyl-1H-5-methylpyrazole (from Step C), 60 mL of 10% aqueous sodium hydroxide, 360 mL of ethanol, and 135 mL of water was heated at reflux for a period of 2.75 hours. After being cooled, the solvents were evaporated under reduced pressure, leaving a residue which was dissolved in water. After being extracted once with diethyl ether, the aqueous solution was acidified with concentrated hydrochloric acid. A tacky solid precipitated from the solution. After standing for more than two days, this orange-yellow solid was filtered from the water and washed with additional water, yielding 6.9 g of 1-(3-chloro-5-trifluoromethyl-2-pyridyl)-4-carboxy-1H-5-methylpyrazole after being dried. The NMR spectrum was consistent with the proposed structure.

Step E Synthesis of 1-(3-chloro-5-trifluoromethyl-2-pyridyl)-4-cyano-1H-5-methylpyrazole A solution of 6.9 g (0.023 mole) of 1-(3-chloro-5-trifluoromethyl-2-pyridyl)-4-carboxy-1H-5-methylpyrazole in 26.9 g (0.226 mole) of thionyl chloride was heated at reflux for 45 minutes. After the reaction mixture was cooled, the excess thionyl chloride was evaporated under reduced pressure, leaving a dark red residue. To this residue were added sequentially 2.64 g (0.0275 mole) of sulfamide and 25 mL of warm sulfolane. The resulting solution was heated at 110° C. for 1.5 hours, after which it was poured into a 3.3% aqueous solution of sodium hydroxide. After the mixture was stirred for 30 minutes, the slurry that had formed was filtered, and the collected solid was washed with water. After being air-dried, the brown solid, 1-(3-chloro-5-trifluoromethyl-2-pyridyl)-4-cyano-1H-5-methylpyrazole, weighed 5.41 g. The NMR spectrum was consistent with the proposed structure.

Step F Synthesis of 1-(3-chloro-5-trifluoromethyl-2-pyridyl)-4-cyano-1H-5-bromomethylpyrazole A mixture of 9.91 g (0.0346 mole) of 1-(3-chloro-5-trifluoromethyl-2-pyridyl)-4-cyano-1H-5-methylpyrazole and 6.16 g (0.0346 mole) of N-bromosuccinimide in 85 mL of carbon tetrachloride was simultaneously heated at reflux and irradiated with a 150 watt heat lamp for four hours. NMR analysis showed that no reaction had occurred during this period. The reaction was stirred for 62 hours with no further illumination or heating. An additional 2 g (0.01 mole) of N-bromosuccinimide was added to the reaction mixture, and the walls of the flask were scraped to remove adhering solids and improve the penetration of the light. Heating and irradiation were resumed for 24 hours, at which time NMR analysis of an aliquot showed that the reaction had gone to completion. The slurry was diluted with additional carbon tetrachloride and then filtered. The filtrate was evaporated under reduced pressure, leaving 13.0 g of 1-(3-chloro-5-trifluoromethyl-2-pyridyl)-4-cyano-1H-5-bromomethylpyrazole as a viscous, red oil. This oil subsequently solidified into a waxy solid.

Step G Synthesis of N-[1-(3-chloro-5-trifluoromethyl-2-pyridyl)-4-cyano-1H-5-pyrazolylmethyl]pyridinium bromide In a flask heated to 65° C. by a water bath, 3.90 g (0.0107 mole) of 1-(3-chloro-5-trifluoromethyl-2-pyridyl)-4-cyano-1H-5-bromomethylpyrazole was dissolved in 12.70 g of pyridine. Heating was continued for 4.5 hours, and stirring at room temperature continued for an additional 16 hours. Heating was then resumed at 50° C. for 2.5 hours. At the end of this period analysis of an aliquot by thin layer chromatography indicated that the reaction was complete. The reaction mixture was then diluted with diethyl ether, causing a solid to form. The N-[1-(3-chloro-5-trifluoromethyl-2-pyridyl)-4-cyano-1H-5-pyrazolylmethyl]pyridinium bromide was collected by filtration as a light brown solid weighing 3.17 g. The NMR spectrum was consistent with the proposed structure.

Step H Synthesis of 1-(3-chloro-5-trifluoromethyl-2-pyridyl)-4-cyano-5-(4-dimethylaminophenyl-N-oxyiminomethyl)-1H-pyrazole A slurry of 3.15 g (0.00708 mole) of N-[1-(3-chloro-5-trifluoromethyl-2-pyridyl)-4-cyano-1H-5-pyrazolylmethyl]pyridinium bromide and 1.11 g (0.00737 mole) of N,N-dimethyl-4-nitrosoaniline in 33 mL of ethanol was placed in a flask. To this slurry was added a solution of 5.54 g (0.0407 mole) of potassium carbonate in 20 mL of water. The color of the slurry changed from green to yellow brown at the time of this addition. After stirring for seven hours, the reaction mixture was filtered, and the filter cake was washed with ethanol. The product, 1-(3-chloro-5-trifluoromethyl-2-pyridyl)-4-cyano-5-(4-dimethylaminophenyl-N-oxyiminomethyl)-1H-pyrazole, was recovered as an orange solid weighing 2.44 g. The NMR spectrum was consistent with the proposed structure.

Step I Synthesis of 1-(3-chloro-5-trifluoromethyl-2-pyridyl)-4-cyano-1H-5-formylpyrazole A slurry of 2.44 g (0.0056 mole) of 1-(3-chloro-5-trifluoromethyl-2-pyridyl)-4-cyano-5-(4-dimethylaminophenyl-N-oxyiminomethyl)-1H-pyrazole in 85 mL of ethyl acetate was placed in a separatory funnel. To this funnel was then added 100 mL of cold, 6N hydrochloric acid. The mixture was shaken for five minutes during which the slurry disappeared, becoming a solution. The organic layer was separated from the aqueous layer. The latter layer was extracted three times with ethyl acetate. A saturated aqueous solution of sodium chloride (50 mL) was added to the aqueous layer, and the resulting mixture was extracted once with ethyl acetate. All of the extracts were combined with the organic layer, and the combined organic solution was washed with a saturated aqueous solution of sodium chloride. The organic solution was dried over anhydrous magnesium sulfate, filtered, and the solvent evaporated under reduced pressure, leaving a yellow oil weighing 3.10 g as a residue. This residue was passed through a six inch column of silica gel, eluting with ethyl acetate/hexanes (1:2). The product-containing fractions were combined, and the solvent was evaporated under reduced pressure, yielding 0.87 g of 1-(3-chloro-5-trifluoromethyl-2-pyridyl)-4-cyano-1H-5-formylpyrazole as a yellow oil. After standing, this oil solidified. The NMR spectrum of this oil was consistent with the proposed structure.

Step J Synthesis of 2-aminooxypropionic Acid

In a flask was placed 20.46 g (0.3646 mole) of potassium hydroxide in 250 mL of ethanol. In one portion 25.00 g (0.1823 mole) of benzohydroxamic acid was added to the flask, and, a solution of 33.00 g (0.1823 mole) of ethyl 2-bromopropionate in 125 mL of ethanol was added dropwise to the reaction mixture. Upon completion of addition, the reaction mixture was stirred for about 16 hours at room temperature, after which it was filtered to remove the solids that had formed. The solvent was evaporated under reduced pressure, and the viscous oil that remained was dissolved in 80% aqueous ethanol. Sufficient 10% sulfuric acid was added to this solution to make the pH=4. The solution was filtered, and the solvents were evaporated under reduced pressure, leaving a residue. To this residue was added 250 mL of 5% hydrochloric acid, and the resulting mixture was heated on a steam bath for two hours. After being cooled, this mixture was filtered, and the filtrate was concentrated under reduced pressure. The residue was dissolved in 250 mL of ethanol. This solution was filtered to remove any insoluble material, and the filtrate was evaporated under reduced pressure. The residue was dissolved in 50 mL of absolute ethanol, and diethyl ether was added to this solution to promote crystallization. This was unsuccessful, and the solvents were evaporated under reduced pressure, leaving a yellow, waxy solid as residue. This solid was recrystallized from a mixture of ethanol and diethyl ether. The white solid, 2-aminooxypropionic acid, which was recovered from the recrystallization weighed 2.25 g; mp 163°–165° C. The NMR spectrum was consistent with the proposed structure. A second crop of crystals formed, yielding an additional 9.15 g of 2-aminooxypropionic acid; mp 164°–166° C. The NMR spectrum of this material was also consistent with the proposed structure.

Step K Synthesis of 2-[[1-(3-chloro-5-trifluoromethyl-2-pyridyl)-4-cyano-1H-5-pyrazolyl]methyliminooxy]propionic acid (Compound 1)

In a flask were placed 0.87 g (0.029 mole) of 1-(3-chloro-5-trifluoromethyl-2-pyridyl)-4-cyano-1H-5-formylpyrazole and 0.49 g (0.0035 mole) of 2-aminooxypropionic acid in 20 mL of tetrahydrofuran and 7 mL of water. This mixture was heated at reflux for five hours. The solvents were then evaporated under reduced pressure, leaving a residue which was dissolved in ethyl acetate. This solution was washed with water, dried over anhydrous magnesium sulfate, and filtered. The solvent was evaporated from the filtrate under reduced pressure, leaving 0.93 g of 2-[[1-(3-chloro-5-trifluoromethyl-2-pyridyl)-4-cyano-1H-4-pyrazolyl]methyliminooxy]propionic acid as a yellow oil which solidified on standing. The NMR spectrum was consistent with the proposed structure.

EXAMPLE 2

Methyl
2-[[1-(3-Chloro-5-Trifluoromethyl-2-Pyridyl)-4-Cyano-1H-5-Pyrazolyl]Methyliminooxy]Propionate
(Compound 2)

In a flask were placed 0.1 g (0.0003 mole) of 2-[[1-(3-chloro-5-trifluoromethyl-2-pyridyl)-4-cyano-1H-4-pyrazolyl]methyliminooxy]propionic acid and a catalytic amount of p-toluenesulfonic acid in 8 mL of methanol. This mixture was heated at reflux with stirring for two hours after which the methanol was evaporated under reduced pressure, leaving an amber oil weighing 0.22 g. Washing this oil with water failed to cause the formation of a solid. The oil was then dissolved in ethyl acetate, and this solution was washed with water. The solution was dried over anhydrous magnesium sulfate, filtered, and the solvent evaporated from the filtrate under reduced pressure, leaving 0.09 g of methyl 2-[[1-(3-chloro-5-trifluoromethyl-2-pyridyl)-4-cyano-1H-5-pyrazolyl]methyliminooxy]propionate as an amber oil. The NMR spectrum was consistent with the proposed structure.

EXAMPLE 3

2-[[1-(2,6-Dichloro-4-Trifluoromethylphenyl)-4-Cyano-1H-5-Pyrazolyl]Methyliminooxy]Propionic Acid (Compound 23)

Step A Synthesis of 2,6-dichloro-4-trifluoromethylphenylhydrazine

A solution of 99.14 g (0.431 mole) of 2,6-dichloro-4-trifluoromethylaniline in 530 mL of glacial acetic acid was placed in a flask and warmed to 55° C. Simultaneously, a mixture of 34.6 g (0.494 mole) of sodium nitrite in 254 mL of concentrated sulfuric acid was prepared by adding the sodium nitrite to the sulfuric acid in a portionwise manner while maintaining the temperature at or below 33° C. The latter mixture was added to the flask in portions while the temperature of the reaction mixture was kept at 62°–64° C. for the first half of the addition. The temperature was reduced to 55°–62° C. during the second half of the addition. Upon completion of this addition, which required 80 minutes, the mixture was cooled to 40° C. with stirring and then rapidly cooled to 0° C. with a dry ice/isopropanol bath. Dropwise, a solution of 378.2 g (1.676 moles) of tin(II) chloride dihydrate in 323 mL of concentrated hydrochloric acid was added to the reaction mixture while maintaining the temperature at −5° to 5° C. This addition required 50 minutes. The reaction mixture was warmed to room temperature and filtered, yielding a moist, pasty solid. This solid was added to 1.1 L of 30% ammonium hydroxide in which there was some ice. This mixture was stirred for 95 minutes and then filtered. The filter cake was transferred to a large beaker, where it was triturated five times with 400 mL of diethyl ether. Each time, the diethyl ether extract was decanted from the solid, and these extracts were combined. The combined extracts were washed once with water, dried over anhydrous magnesium sulfate, filtered, and the solvent evaporated under reduced pressure, yielding 63 g of 2,6-dichloro-4-trifluorophenylhydrazine as a pale yellow, crystalline solid. The NMR spectrum was consistent with the proposed structure. The filter cake was triturated two more times with 400 mL of diethyl ether. These extracts were treated in the same manner as the previous ones, yielding an additional 7.2 g of 2,6-dichloro-4-trifluoromethylphenylhydrazine. The NMR spectrum of this sample was also consistent with the proposed structure.

Step B Synthesis of Ethyl 2-dimethylaminomethyleneacetoacetate

A mixture of 200 g (1.68 moles) of N,N-dimethylformamide dimethyl acetal, 145.68 g (1.12 moles) of ethyl acetoacetate, and 0.5 g (0.003 mole) of p-toluenesulfonic acid monohydrate was heated in a water bath with stirring for three hours. The color of the reaction mixture changed progressively from orange to red and finally to brown. Heating was discontinued, and the reaction mixture was allowed to sit at room temperature for approximately 18 hours. At the conclusion of this period, the mixture was distilled under vacuum, and six fractions having a boiling point in the range 145°–150° C. were analyzed by NMR spectroscopy. The NMR spectrum of each fraction was consistent with the proposed structure. These fractions were combined, yielding a total of 148.51 g of ethyl-2-dimethylaminomethyleneacetoacetate.

Step C Synthesis of 1-(2,6-dichloro-4-trifluoromethylphenyl)-4-ethoxycarbonyl-1H-5-methylpyrazole A solution of 41.4 g (0.17 mole) of 2,6-dichloro-4-trifluoromethylphenylhydrazine and 31.6 g (0.171 mole) of ethyl 2-dimethylaminomethyleneacetoacetate in 800 mL of ethanol was heated at reflux for two hours. At the conclusion of this period, the solvent was immediately evaporated under reduced pressure, leaving a red oil weighing 62.3 g as a residue. This residue was dissolved in methylene chloride. This solution was washed successively with 10% hydrochloric acid, a saturated aqueous solution of sodium bicarbonate, and finally water. The solution was dried over anhydrous magnesium sulfate, filtered, and the solvent was evaporated under reduced pressure, leaving 59.2 g of 1-(2,6-dichloro-4-trifluoromethylphenyl)-4-ethoxycarbonyl-1H-5-methylpyrazole as a red oil. This oil later solidified to a waxy solid. The NMR spectrum was consistent with the proposed structure.

Step D Synthesis of 1-(2,6-dichloro-4-trifluoromethylphenyl)-4-carboxy-1H-5-methylpyrazole By the method of Example 1, Step D, 58.1 g (0.158 mole) of 1-(2,6-dichloro-4-trifluoromethylphenyl)-4-ethoxycarbonyl-1H-5-methylpyrazole and 10 g (0.25 mole) of sodium hydroxide were reacted in 325 mL of ethanol and 175 mL of water, yielding 51.55 g of 1-(2,6-dichloro-4-trifluoromethylphenyl)-4-carboxy-1H-5-methylpyrazole. The NMR spectrum was consistent with the proposed structure.

Step E Synthesis of 1-(2,6-dichloro-4-trifluoromethylphenyl)-4-cyano-1H-5-methylpyrazole By the method of Example 1, Step E, 49.5 g (0.146 mole) of 1-(2,6-dichloro-4-trifluoromethylphenyl)-4-carboxy-1H-5-methylpyrazole, 171.6 g (1.44 moles) of thionyl chloride, and 19.14 g (0.199 mole) of sulfamide were reacted in 165 mL of sulfolane, yielding 40.9 g of 1-(2,6-dichloro-4-trifluoromethylphenyl)-4-cyano-1H-5-methylpyrazole as a tan solid. The NMR spectrum was consistent with the proposed structure.

Step F Synthesis of 1-(2,6-dichloro-4-trifluoromethylphenyl)-4-cyano-1H-5-bromomethylpyrazole By the method of Example 1, Step F, 39.2 g (0.123 mole) of 1-(2,6-dichloro-4-trifluoromethylphenyl)-4-cyano-1H-5-methylpyrazole was reacted with 24.15 g (0.135 mole) of N-bromosuccinimide in 800 mL of carbon tetrachloride, yielding 49.6 g of 1-(2,6-dichloro-4-trifluoromethylphenyl)-4-cyano-1H-5-bromomethylpyrazole as somewhat turbid dark, reddish oil. The NMR spectrum was consistent with the proposed structure, but indicated that the purity was only 64.4%.

Step G Synthesis of N-[1-(2,6-dichloro-4-trifluoromethylphenyl)-4-cyano-1H-5-pyrazolylmethyl]pyridinium Bromide By the method of Example 1, Step G, 24.1 g of the 64.4% 1-(2,6-dichloro-4-trifluoromethylphenyl)-4-cyano-1H-5-bromomethylpyrazole (estimated to be 15.7 g, 0.039 mole of pure material) was reacted with 120 mL of pyridine, yielding 18.2 g of N-[1-(2,6-dichloro-4-trifluoromethylphenyl)-4-cyano-1H-5-pyrazolylmethyl]pyridinium bromide as a solid. The NMR spectrum was consistent with the proposed structure.

Step H Synthesis of 1-(2,6-dichloro-4-trifluoromethylphenyl)-4-cyano-1H-5-(4-dimethylaminophenyl-N-oxyiminomethyl)pyrazole By the method of Example 1, Step H, 18.2 g (0.038 mole) of N-[1-(2,6-dichloro-4-trifluoromethylphenyl)-4-cyano-1H-5-pyrazolylmethyl]pyridinium bromide, 5.86 g (0.039 mole) of N,N-dimethyl-4-nitrosoaniline, and 29.35 g (0.21 mole) of potassium carbonate were reacted in 175 mL of ethanol, yielding 14.8 g of 1-(2,6-dichloro-4-trifluoromethylphenyl)-4-cyano-1H-5-(4-dimethylaminophenyl-N-oxyiminomethyl)pyrazole as a solid. The NMR spectrum was consistent with the proposed structure.

Step I Synthesis of 1-(2,6-dichloro-4-trifluoromethylphenyl)-4-cyano-1H-5-formylpyrazole By the method of Example 1, Step I, 14.6 g (0.031 mole) of 1-[1-(2,6-dichloro-4-trifluoromethylphenyl)-4-cyano-1H-5-(4-dimethylaminophenyl-N-oxyiminomethyl)pyrazole was reacted with 600 mL of 6N hydrochloric acid in 600 mL of ethanol, yielding 5.51 g of 1-(2,6-dichloro-4-trifluoromethylphenyl)-4-cyano-1H-5-formylpyrazole as a bright yellow solid, mp 128°-131° C. The NMR spectrum was consistent with the proposed structure.

Step J Synthesis of 2-[[1-(2,6-dichloro-4-trifluoromethylphenyl)-4-cyano-1H-5-pyrazolyl]methyliminooxy]propionic Acid (Compound 23)

By the method of Example 1, Step K, 0.60 g (0.0018 mole) of 1-(2,6-dichloro-4-trifluoromethylphenyl)-4-cyano-1H-5-formylpyrazole and 0.33 g (0.0023 mole) of 2-aminooxypropionic acid were reacted in 12 mL of tetrahydrofuran and 4 mL of water, yielding 0.64 g of 2-[[1-(2,6-dichloro-4-trifluoromethylphenyl)-4-cyano-1H-5-pyrazolyl]methyliminooxy]propionic acid as a yellow oil. The NMR spectrum was consistent with the proposed structure. This reaction was repeated to prepare additional product for the preparation of derivatives of this acid.

EXAMPLE 4

3-Chlorophenylmethyl 2-[[1-(2,6-Dichloro-4-Trifluoromethylphenyl)-4-Cyano-1H-5-Pyrazolyl]-Methyliminooxy]Propionate (Compound 31)

A mixture of 0.75 g (0.0018 mole) of 2-[[1-2,6-dichloro-4-trifluoromethylphenyl)-4-cyano-1H-5-pyrazolyl]methyliminooxy]propionic acid, 0.37 g (0.0018 mole) of 3-chlorophenylmethyl bromide, and 0.30 g (0.0022 mole) of potassium carbonate in 35 mL of toluene was heated at reflux for 75 minutes. Analysis by thin layer chromatography showed little reaction. A few crystals of potassium iodide were added, and heating was resumed. Two hours later an additional 0.10 g (0.0005 mole) of 3-chlorophenylmethyl bromide was added. After 80 minutes, heating was stopped, and the solvents were evaporated under reduced pressure, leaving a residue. This residue was dissolved in diethyl ether, and the ether solution was washed in succession with water, a saturated aqueous solution of sodium bicarbonate, water, and a saturated aqueous solution of sodium chloride. The solution was then dried over anhydrous magnesium sulfate, filtered, and the solvent evaporated under reduced pressure, leaving an oil weighing 0.8 g as a residue. This residue was passed through a column of silica gel, eluting first with hexanes/methylene chloride (20:80) and finally with pure methylene chloride. The product-containing fractions were combined, and the solvent was evaporated under reduced pressure, leaving 0.37 g of 3-chlorophenylmethyl 2-[[1-(2,6-dichloro-4-trifluoromethylphenyl)-4-cyano-1H-5-pyrazolyl]methyliminooxy]propionate as a viscous oil. The NMR spectrum was consistent with the proposed structure.

EXAMPLE 5

Methyl 2-[[1-(2,6-Dichloro-4-Trifluoromethylphenyl)-4-Cyano-1H-5-Pyrazolyl](Methoxymethyl)Iminooxy]Acetate (Compound 66, Z Isomer; Compound 67, E Isomer)

Step A Synthesis of 1-(2,6-dichloro-4-trifluoromethylphenyl)-4-cyano-1H-5-pyrazolylcarboxylic Acid A solution of 12 g (0.036 mole) of 1-(2,6-dichloro-4-trifluoromethylphenyl)-4-cyano-1H-5-formylpyrazole in 750 mL of acetone was cooled to −5° to 5° C. with stirring. A solution of 7.11 g (0.0450 mole) of potassium permanganate and 13.8 g (0.0515 mole) of disodium hydrogen phosphate heptahydrate in 300 mL of water was added dropwise to the cooled solution during a 15 minute period while the temperature was held at approximately 0° C. Upon completion of addition, the cooling bath was removed, and stirring was continued for approximately 20 hours at ambient temperature. At the conclusion of the period, 18 g (0.17 mole) of sodium hydrogen sulfite was added to the reaction mixture. This mixture was stirred for about an hour, after which Celite filter aid was added and the mixture filtered. Most of the acetone was evaporated from the filtrate under reduced pressure, and the aqueous residue was acidified with 20% hydrochloric acid, causing a solid to precipitate. The solid was recovered by filtration and, after being air-dried, was dissolved in a mixture of acetone and methylene chloride. This solution was dried over anhydrous magnesium sulfate, filtered, and the solvent evaporated from the filtrate under reduced pressure, leaving 12.2 g of 1-(2,6-dichloro-4-trifluoromethylphenyl)-4-cyano-1H-5-pyrazolylcarboxylic acid as a white solid. The NMR spectrum was consistent with the proposed structure.

Step B Synthesis of 1-(2,6-dichloro-4-trifluoromethylphenyl)-4-cyano-1H-5-pyrazolylcarboxylic Acid Chloride A slurry of 12.0 g (0.0343 mole) of 1-(2,6-dichloro-4-trifluoromethylphenyl)-4-cyano-1H-5-pyrazolylcarboxylic acid in 30 mL (49 g, 0.41 mole) of thionyl chloride was heated at gentle reflux for approximately 62 hours, after which it had become a dark solution. This solution was cooled, and the excess thionyl chloride was evaporated under reduced pressure, leaving a residue. Petroleum ether was added to this residue, causing a precipitate, which, upon filtration, yielded 7.4 g of 1-(2,6-dichloro-4-trifluoromethylphenyl)-4-cyano-1H-5-pyrazolylcarboxylic acid chloride as a solid, mp 100°–102° C. The NMR spectrum was consistent with the proposed structure. A second crop of tacky crystals was obtained by chilling the filtrate obtained when the product was isolated by filtration. The NMR spectrum of the second crop of crystals was consistent with the proposed structure, but showed also that it was contaminated with some starting material.

Step C Synthesis of N-methoxycarbonylmethoxy-1-(2,6-dichloro-4-trifluoromethylphenyl)-4-cyano-1H-5-pyrazolylcarboxamide A solution of 2.31 g (0.022 mole) of methyl aminooxyacetate and 2.53 g (0.025 mole) of triethylamine in 70 mL of diethyl ether was cooled to −5° to 0° C. While this temperature was maintained, a solution of 7.4 g (0.020 mole) of 1-(2,6-dichloro-4-trifluoromethylphenyl)-4-cyano-1H-5-pyrazolylcarboxylic acid chloride in 105 mL of tetrahydrofuran was added to the cooled solution during a 20 minute period. Upon completion of addition, the cooling bath was removed, and the resulting slurry was stirred at ambient temperature for 125 minutes. The slurry was filtered, and the filtrate was evaporated under reduced pressure, leaving a residue. This residue was dissolved in ethyl acetate, and this solution was washed twice with an aqueous solution of sodium chloride. The solution was then dried over anhydrous magnesium sulfate, filtered, and the solvent evaporated from the filtrate under reduced pressure, leaving a tacky solid residue weighing 8.54 g. This solid was triturated with petroleum ether for a period of approximately 17 hours. The resulting N-methoxycarbonylmethoxy-1-(2,6-dichloro-4-trifluoromethylphenyl)-4-cyano-1H-5-pyrazolylcarboxamide, weighing 7.5 g, was recovered by filtration. The NMR spectrum was consistent with the proposed structure.

Step D Synthesis of methyl 2-[[1-(2,6-dichloro-4-trifluoromethylphenyl)-4-cyano-1H-5-pyrazolyl](methoxymethyl)-iminooxy]acetate (E isomer) (Compound 67)

To a solution of 1.32 g (0.0030 mole) of N-methoxycarbonylmethoxy-1-(2,6-dichloro-4-trifluoromethylphenyl)-4-cyano-1H-5-pyrazolylcarboxamide in 15 mL of N,N-dimethylformamide was added 0.676 g (0.0049 mole) of potassium carbonate, and this mixture was warmed to 65°–70° C. A solution of 0.676 g (0.0036 mole) of methyl p-toluenesulfonate in 6 mL of N,N-dimethylformamide was added dropwise to the heated solution during a 15 minute period. Heating was continued for two hours, and the reaction mixture was then cooled and poured into 400 mL of water. Aqueous 10% lithium chloride solution was added to aid in phase separation during extraction with ethyl acetate. Three additional extractions were performed using ethyl acetate to which petroleum ether had been added. All extracts were combined, and the combined extracts were washed three times with a 10% aqueous solution of lithium chloride. The extracts were dried over anhydrous magnesium sulfate, filtered, and the filtrate evaporated under reduced pressure, yielding a residue weighing 1.1 g. This residue was combined with a similar residue from a previous experiment, and this combination was purified by thin layer plate preparative chromatography, eluting with ethyl acetate/heptane (1:1). Extracted from the product-containing band was 0.12 g of methyl 2-[[1-(2,6-dichloro-4-trifluoromethylphenyl)-4-cyano-1H-5-pyrazolyl](methoxymethyl)iminooxy]acetate (E isomer); mp 117°–120° C. The NMR spectrum was consistent with the proposed structure.

Elemental Analysis:

calculated: C, 42.59; H, 2.46; N, 12.42. found: C, 42.76; H, 2.30; N, 12.57.

The above reaction was repeated using 6.5 g (0.015 mole) of N-methoxycarbonylmethoxy-1-(2,6-dichloro-4-trifluoromethylphenyl)-4-cyano-1H-5-pyrazolylcarboxamide, 3.34 g (0.0179 mole) of methyl p-toluenesulfonate, 3.34 g (0.024 mole) of potassium carbonate, and 110 mL of N,N-dimethylformamide. The ethyl acetate extract containing the product was evaporated under reduced pressure, leaving a viscous oil weighing 5.91 g as a residue. This oil was passed through a column of Silica Gel 60, eluting with ethyl acetate/heptane (1:1). The fractions containing methyl 2-[[1-(2,6-dichloro-4-trifluoromethylphenyl)-4-cyano-1H-5-pyrazolyl](methoxymethyl)iminooxy]acetate (E isomer) were combined and evaporated under reduced pressure, yielding 1.48 of this white solid. The NMR was consistent with the product obtained in the preceding preparation. Fractions containing the other isomer were also combined and evaporated under reduced pressure, leaving 0.23 g of methyl 2-[[1-(2,6-dichloro-4-trifluoromethylphenyl)-4-cyano-1H-5-pyrazolyl](methoxymethyl)iminooxy]acetate (Z isomer), Compound 66, as an oil. The NMR spectrum of this product was consistent with the proposed structure.

EXAMPLE 6

Methyl 2-[[1-(2,4,6-trichlorophenyl)-4-cyano-1H-5-pyrazolyl]-methyliminooxy]propionate (Compound 71)

Step A Synthesis of 1-(2,4,6-trichlorophenyl)-4-ethoxycarbonyl-5-methyl-1H-pyrazole By the method of Example 3, Step C, 25.9 g (0.122 mole) of 2,4,6-trichlorophenylhydrazine and 22.7 g (0.123 mole) of ethyl 2-dimethylaminomethyleneacetoacetate were reacted in ethanol, yielding 1-(2,4,6-trichlorophenyl)-4-ethoxycarbonyl-5-methyl-1H-pyrazole as tan solid; mp 112.5°–113° C. The NMR spectrum was consistent with the proposed structure.

Step B Synthesis of 1-(2,4,6-trichlorophenyl)-4-carboxy-5-methyl-1H-pyrazole

By the method of Example 1, Step D, 40.0 g (0.12 mole) of 1-(2,4,6-trichlorophenyl)-4-ethoxycarbonyl-5-methyl-1H-pyrazole and 5.75 g (0.14 mole) of sodium hydroxide were reacted in 40 mL of ethanol and 30 mL of water, yielding 26.2 g of 1-(2,4,6-trichlorophenyl)-4-carboxy-5-methyl-1H-pyrazole as a light tan solid; mp 184°–186.5° C. The NMR spectrum was consistent with the proposed structure.

Step C Synthesis of 1-(2,4,6-trichlorophenyl)-4-cyano-5-methyl-1H-pyrazole

By the method of Example 1, Step E, 25.6 g (0.0838 mole) of 1-(2,4,6-trichlorophenyl)-4-carboxy-5-methyl-1H-pyrazole, 114.3 g (0.961 mole) of thionyl chloride, and 12.7 g (0.132 mole) of sulfamide were reacted in 100 mL of sulfolane, yielding 18.25 g of 1-(2,4,6-trichlorophenyl)-4-cyano-5-methyl-1H-pyrazole as an oil which subsequently solidified. The NMR spectrum was consistent with the proposed structure.

Step D Synthesis of 1-(2,4,6-trichlorophenyl)-4-cyano-5-bromomethyl-1H-pyrazole

By the method of Example 1, Step F, 18 g (0.063 mole) of 1-(2,4,6-trichlorophenyl)-4-cyano-5-methyl-1H-pyrazole and 11.5 g (0.065 mole) of N-bromosuccinimide were reacted in 200 mL of carbon tetrachloride, yielding more than 20 g of a mixture of 1-(2,4,6-trichlorophenyl)-4-cyano-5-methyl-1H-pyrazole and 1-(2,4,6-trichlorophenyl)-4-cyano-5-bromomethyl-1H-pyrazole. This mixture was used without further purification in Step E.

Step E Synthesis of N-[1-(2,4,6-trichlorophenyl)-4-cyano-1H-pyrazol-5-ylmethyl]pyridinium Bromide The method of Example 1, Step G, using 20.7 g of the mixture from Step D above dissolved in 90 mL of warm pyridine, yielded 11.1 g of N-[1-(2,4,6-trichlorophenyl)-4-cyano-1H-pyrazol-5-ylmethyl]pyridinium bromide, which was used without further purification in Step F.

Step F Synthesis of 1-(2,4,6-trichlorophenyl)-4-cyano-1H-5-(4-dimethylaminophenyl-N-oxyiminomethyl)-1H-pyrazole By the method of Example 1, Step H, 7.76 g (0.017 mole) of N-[1-(2,4,6-trichlorophenyl)-4-cyano-1H-pyrazol-5-ylmethyl]pyridinium bromide from Step E above, 2.72 g (0.018 mole) of N,N-dimethyl-4-nitrosoaniline, and 13.7 g (0.10 mole) of potassium carbonate were reacted in 82 mL of ethanol, yielding 6.43 g of 1-(2,4,6-trichlorophenyl)-4-cyano-1H-5-(4-dimethylaminophenyl-N-oxyiminomethyl)-1H-pyrazole as an orange powder; mp 199°–200° C. The NMR spectrum was consistent with the proposed structure.

Step G Synthesis of 1-(2,4,6-trichlorophenyl)-4-cyano-5-formyl-1H-pyrazole

By the method of Example 1, Step I, 6.24 g (0.014 mole) of 1-(2,4,6-trichlorophenyl)-4-cyano-1H-5-(4-dimethylaminophenyl-N-oxyiminomethyl)-1H-pyrazole and 240 mL of 6N hydrochloric acid were reacted in 100 mL of diethyl ether, yielding 3.04 g of 1-(2,4,6-trichlorophenyl)-4-cyano-5-formyl-1H-pyrazole as a pale pink solid; mp 152.5° C. The NMR spectrum was consistent with the proposed structure.

Step H Synthesis of 2-[[1-(2,4,6-trichlorophenyl)-4-cyano-1H-pyrazolyl]methyliminooxy]propionic Acid (Compound 70)

By the method of Example 1, Step K, 2.58 g (0.0086 mole) of 1-(2,4,6-trichlorophenyl)-4-cyano-5-formyl-1H-pyrazole and 1.35 g (0.0095 mole) of 2-aminooxypropionic acid hydrochloride were reacted in 40 mL of tetrahydrofuran, yielding 2.52 g of 2-[[1-(2,4,6-trichlorophenyl)-4-cyano-1H-pyrazolyl]methyliminooxy]propionic acid as a peach-colored solid; mp 107.5°–110.5° C. The NMR spectrum was consistent with the proposed structure.

Step I Synthesis of methyl 2-[[1-(2,4,6-trichlorophenyl)-4-cyano-1H-pyrazolyl]methyliminooxyl]propionate (Compound 71)

By the method of Example 2, 0.32 g (0.00083 mole) of 2-[[1-(2,4,6-trichlorophenyl)-4-cyano-1H-pyrazolyl]methyliminooxy]propionic acid was reacted with 30 mL of methanol in the presence of catalyst amount p-toluenesulfonic acid monohydrate, yielding 0.37 g of methyl 2-[[1-(2,4,6-trichlorophenyl)-4-cyano-1H-pyrazolyl]methyliminooxy]propionate as a pink solid; mp 111°–113.5° C. The NMR spectrum was consistent with the proposed structure.

Representative compounds of the invention prepared by the methods exemplified above are shown in Table 1. Characterizing data of these compounds are given in Table 2.

Herbicidal Activity

The 2-(1-aryl-4-cyano-5-pyrazolymethyleneiminooxy)alkanoic acid derivatives of this invention were tested in pre- and postemergence evaluations on a variety of broadleaf and grasseous crops and weeds. The test species used to demonstrate herbicidal activity include soybean (*Glycine max* var. Williams), field corn (*Zea mays* var. Agway 425X), wheat (*Triticum aestivum* var. Wheaton), morningglory (*Ipomoea lacunosa* or *Ipomoea hederacea*), velvetleaf (*Abutilon theophrasti*), green foxtail (*Setaria viridis*), Johnsongrass (*Sorghum halepense*), blackgrass (*Aloepecurus myosuroides*), common chickweed (*Stellaria media*), and common cocklebur (*Xanthium pensylvanicum*).

Procedure

For preemergence testing, two disposable fiber flats (8 cm × 15 cm × 25 cm) for each rate of application of each candidate herbicide were filled to an approximate depth of 6.5 cm with steam-sterilized sandy loam soil. The soil was leveled and impressed with a template to provide five evenly spaced furrows 13 cm long and 0.5 cm deep in each flat. Seeds of soybean, wheat, corn, green foxtail, and Johnsongrass were planted in the furrows of the first flat, and seeds of velvetleaf, morningglory, common chickweed, cocklebur, and blackgrass were planted in the furrows of the second flat. The five-row template was employed to press the seeds firmly into place. A topping soil of equal portions of sand and sandy loam soil was placed uniformly on top of each flat to a depth of approximately 0.5 cm. Flats for postemergence testing were prepared in the same manner except that they were planted 8–12 days prior to the preemergence flats and were placed in a greenhouse and watered, thus allowing the seeds to germinate and the foliage to develop.

A stock solution of the candidate herbicide was prepared by dissolving a predetermined weight of the compound in 20 mL of water/acetone (50/50) containing 0.5% v/v sorbitan monolaurate. Thus for an application rate of up to 3000 g/ha of herbicide, 0.27 g of candidate herbicide was dissolved in 20 mL of the aqueous acetone to prepare the stock solution. A portion (10 mL) was then diluted with water/acetone (50/50) to 45 mL, the volume required to correspond to a spray volume of 1000 L/ha. The remaining stock solution was then used to prepare lower application rates.

For the nominal 0.1 kg/ha rate reported in Tables 3 and 4, 0.3 mL of stock solution was diluted with 45 mL of water/acetone (50/50) to a total volume of spray solution of 45.3 mL. (This dilution actually results in a rate of 0.09 kg/ha, but is reported as 0.1.)

The spray solution (45.3 mL) was sprayed on the four flats simultaneously, i.e., to the surface of the soil of the preemergence flats and to the emerged foliage of the postemergence flats; all flats were placed in the greenhouse, but only the preemergence flats were watered immediately. The foliage of the post-emergence flats was kept dry for 24 hours after which regular watering commenced. Phytotoxicity data were recorded 17–21 days after the chemical was applied.

Phytotoxicity data are taken as percent control. Percent control is determined by a method similar to the 0 to 100 rating system disclosed in "Research Methods in Weed Science," 2nd ed., B. Truelove, Ed.; Southern Weed Science Society; Auburn University, Auburn, Ala. 1977. The rating system is as follows:

Herbicide Rating System

| Rating Percent Control | Description of Main Categories | Crop Description | Weed Description |
|---|---|---|---|
| 0 | No effect | No crop reduction or injury | No weed control |
| 10 | | Slight discoloration or stunting | Very poor weed control |
| 20 | Slight effect | Some discoloration, stunting or stand loss | Poor weed control |
| 30 | | Crop injury more pronounced but not lasting | Poor to deficient weed control |
| 40 | | Moderate injury, crop usually recovers | Deficient weed control |
| 50 | Moderate effect | Crop injury more lasting, recovery doubtful | Deficient to moderate weed control |
| 60 | | Lasting crop injury, no recovery | Moderate weed control |
| 70 | | Heavy injury and stand loss | Control somewhat less than satisfactory |
| 80 | Severe | Crop nearly destroyed, a few survivors | Satisfactory to good weed control |
| 90 | | Only occasional live plants left | Very good to excellent control |
| 100 | Complete effect | Complete crop destruction | Complete weed destruction |

Herbicidal data are given for the compounds of the invention in Tables 3 and 4. The test compounds are identified in the tables by numbers that correspond to those in Table 1.

The compounds of this invention are particularly useful as preemergence herbicides owing to crop selectivity for some compounds that is lacking when they are applied postemergently. Compounds that show particularly good preemergence activity and crop tolerance at lower rates of application are Compounds 2, 5, 15, 24, 31, 47, and 50.

For herbicidal application the active compounds of the invention are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and post-emergence herbicides, are in the form of finely divided particles which disperse readily in water or other dispersant. A wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, and 1.0 part of sodium lignosulfonate and 0.3 part of sulfonated aliphatic polyester as wetting agents. Frequently additional wetting agent(s) and/or oil will be added to the tank mix for postemergence application to facilitate dispersion on the foilage and absorption by the plant.

Other useful formulations for herbicidal applications are emulsifiable concentrates (ECs), which are homogeneous liquid compositions dispersible in water or other dispersant, and may consist entirely of the herbical compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing, or emulsifying agents used in agricultural formulations include, but are not limited to, the alkyl and alkylaryl sulfonates and the sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent(s), when used, normally comprises from 1 to 15% by weight of the composition.

Other useful formulations include suspensions of the active ingredient in a relatively non-volatile liquid such as water, corn oil, kerosene, propylene glycol, or other suitable liquid carrier.

Still other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as carbon dioxide, propane, or butane, may also be used. Water-soluble or water-dispersible granule are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful with the present herbicidal compounds. For use by the farmer on the field, the granular formulations, emulsifiable concentrates, flowable concentrates, solutions, etc., may be diluted with water to give a concentration of active ingredient in the range of, say, 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is, of course, employed; the amount may be as low as, e.g., about 10 to 100 g/ha, preferably about 30 to 60 g/ha. For field use, where there are losses of herbicide, higher application rates (e.g., four times the greenhouse testing rates mentioned above) may be employed.

The active herbicidal compounds of this invention may be used in combination with other herbicides, e.g., they may be mixed with, say, a lesser, equal, or larger amount of a known herbicide such as aryloxyalkanoic acid herbicides such as (2,4-dichlorophenoxy)acetic acid (2,4-D), (4-chloro-2-methylphenoxy)acetic acid (MCPA), (+/−)-2-(4-chloro-2-methylphenoxy)-propanoic acid (MCPP); urea herbicides, such as N,N-dimethyl-N'-[4-(1-methylethyl)phenyl]urea (isoproturon); imidazolinone herbicides, such as 2-[4,5-dihydro-4-methyl-4-(1-methylethyl)-5-oxo-1H-imidazol-2-yl]-3-pyridinecarboxylic acid (imazapyr), a reaction product comprising (+/−)-2-[4,5-dihydro-4-methyl-4-(1-methylethyl)-5-oxo-1H-imidazol-2-yl]-4-methylbenzoic acid and (+/−)-2-[4,5-dihydro-4-methyl-4-(1-methylethyl)-5-oxo-1H-imidazol-2-yl]-5-methylbenzoic acid (imazamethabenz), (+/−)-2-[4,5-dihydro-4-methyl-4-(1-methylethyl)-5-oxo-1H-imidazol-2-yl]-5-ethyl-3-pyridinecarboxylic acid (imazethapyr), and (+/−)-2-[4,5-dihydro-4-methyl-4-(1-methylethyl)-5-oxo-1H-imidazol-2-yl]-3-quinolinecarboxylic acid (imazaquin); diphenyl ether herbicides, such as 5-[2-chloro-4-(trifluoromethyl)phenoxy]-2-nitrobenzoic acid (acifluorfen), methyl 5-(2,4-dichlorophenoxy)-2-nitrobenzoate (bifenox), and 5-[2-chloro-4-(trifluoromethyl)phenoxy]-N-(methylsulfonyl)-2-nitrobenzamide (fomasafen); hydroxybenzonitrile herbicides, such as 4-hydroxy-3,5-diiodobenzonitrile (ioxynil), and 3,5-dibromo-4-hydroxybenzonitrile (bromoxynil); sulfonylurea herbicides, such as 2-[[[[(4-chloro-6-methoxy-2-pyrimidinyl)amino]carbonyl]amino]sulfonyl]benzoic acid (chlorimuron), 2-chloro-N-[[(4-methoxy-6-methyl-1,3,5-triazin-2-yl)amino]carbonyl]benzenesulfonamide (chlorsulfuron), 2-[[[[(4,6-dimethoxy-2-pyrimidinyl)amino]carbonyl]amino]sulfonyl]methyl]benzoic acid (bensulfuron), 2-[[[[(4,6-dimethoxy-2-pyrimidinyl)amino]carbonyl]amino]sulfonyl]-1-methyl-1H-pyrazol-4-carboxylic acid (pyrazosulfuron), 3-[[[[(4-methoxy-6-methyl-1,3,5-triazin-2-yl)amino]carbonyl]amino]sulfonyl]-2-thiophenecarboxylic acid (thifensulfuron), and 2-(2-chloroethoxy)-N-[[(4-methoxy-6-methyl-1,3,5-triazin-2-yl)amino]carbonyl]benzenesulfonamide (triasulfuron); 2-(4-aryloxyphenoxy)alkanoic acid herbicides, such as (+/−)-2-[4-[(6-chloro-2-benzoxazolyl)oxy]phenoxy]propanoic acid (fenoxaprop), (+/−)-2-(4-[[5-(trifluoromethyl)-2-pyridinyl]oxy]phenoxy]propanoic acid (fluazifop), (+/−)-2-[4-(6-chloro-2-quinoxalinyl)oxy]phenoxy]propanoic acid (quizalofop), and (+/−)-2-[-(2,4-dichlorophenoxy)phenoxy]propanoic acid (diclofop); benzothiadiazinone herbicides, such as 3-(1-methylethyl)-1H-2,1,3-benzothiadiazin-4(3H)-one 2,2-dioxide (bentazone); 2-chloroacetanilide herbicides, such as N-(butoxymethyl)-2-chloro-2',6'-diethylacetanilide (butachlor); arenecarboxylic acid herbicides, such as 3,6-dichloro-2-methoxybenzoic acid (dicamba); and pyridyloxyacetic acid herbicides, such as [(4-amino-3,5-dichloro-6-fluoro-2-pyridinyl)oxy]acetic acid (fluroxypyr).

It is apparent that various modifications may be made in the formulation and application of the compounds of this invention without departing from the inventive concepts herein as defined in the claims.

TABLE 1

Derivatives of 2-(1-Aryl-4-cyano-5-pyrazolylmethyleneiminooxy)-alkanoic Acids

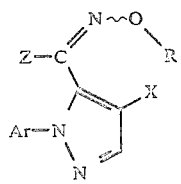

| Compound No | R | | R¹ | Y | R² |
|---|---|---|---|---|---|

When R = Q, Q = $-\underset{R^1}{\overset{}{\text{CH}}}-C(O)-Y-R^2$, Z = H, and Ar = 3-chloro-5-(trifluoromethyl)-2-pyridyl

| | | | | | |
|---|---|---|---|---|---|
| 1 | Q | | CH₃ | O | H |
| 2 | Q | | CH₃ | O | CH₃ |
| 3 | Q | | CH₃ | O | C₂H₅ |
| 4 | Q | | CH₃ | O | i-C₃H₇ |
| 5 | Q | | CH₃ | O | —(CH₂)₂CH₂Cl |
| 6 | Q | | CH₃ | O | —CH₂SCH₃ |
| 7 | Q | | CH₃ | O | —CH₂CN |
| 8 | Q | | CH₃ | O | —CH(CH₃)CN |
| 9 | Q | | CH₃ | O | 2-ethyl-tetrahydrofuryl |
| 10 | Q | | CH₃ | O | —CH₂—C₆H₅ |
| 11 | Q | | CH₃ | O | —CH₂—(3-chlorophenyl) |
| 12 | Q | | CH₃ | O | i-C₃H₇NH₃⁺ |
| 13 | Q | | CH₃ | O | HO(CO₂)₂NH(CH₃)₂⁺ |
| 14 | Q | | CH₃ | NH | —C(CH₃)₂CN |
| 15 | Q | | CH₃ | NH | —S(O)₂CH₃ |
| 16 | Q | | CH₃ | NH | —S(O)₂—CH₂—C₆H₅ |
| 17 | Q | | H | O | H |
| 18 | Q | | H | O | CH₃ |
| 19 | Q | | H | NH | CH₃ |
| 20 | CH₃ | | — | — | — |
| 21 | —CH₂CH=CHCl | | — | — | — |

TABLE 1-continued

Derivatives of 2-(1-Aryl-4-cyano-5-pyrazolylmethyleneiminooxy)-alkanoic Acids

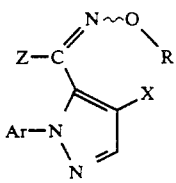

| Compound No | R | R¹ | Y | R² |
|---|---|---|---|---|
| 22 | —CH₂—C≡CH (propargyl-like) | — | — | — |

When R = Q, Q = 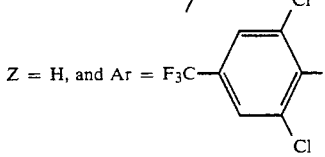

Z = H, and Ar = 2,6-dichloro-4-(trifluoromethyl)phenyl

| Compound No | R | R¹ | Y | R² |
|---|---|---|---|---|
| 23 | Q | CH₃ | O | H |
| 24 | Q | CH₃ | O | CH₃ |
| 25 | Q | CH₃ | O | i-C₃H₇ |
| 26 | Q | CH₃ | O | —(CH₂)₂CH₂Cl |
| 27 | Q | CH₃ | O | —CH₂SCH₃ |
| 28 | Q | CH₃ | O | 2-ethyl-tetrahydrofuran |
| 29 | Q | CH₃ | O | —CH₂—C₆H₅ |
| 30 | Q | CH₃ | O | —CH₂—(2-Cl-C₆H₄) |
| 31 | Q | CH₃ | O | —CH₂—(3-Cl-C₆H₄) |
| 32 | Q | CH₃ | O | —CH₂—(4-Cl-C₆H₄) |
| 33 | Q | CH₃ | O | —CH₂—(3-CH₃-C₆H₄) |

TABLE 1-continued
Derivatives of 2-(1-Aryl-4-cyano-5-pyrazolylmethyleneiminooxy)-alkanoic Acids
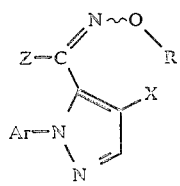
| Compound No | R | $R^1$ | Y | $R^2$ |
|---|---|---|---|---|
| 34 | Q | $CH_3$ | O | -CH$_2$-(2-F,3-Cl-phenyl) |
| 35 | Q | $CH_3$ | O | -CH$_2$-(2,3-Cl$_2$-phenyl) |
| 36 | Q | $CH_3$ | O | -CH$_2$-(2,4-Cl$_2$-phenyl) |
| 37 | Q | $CH_3$ | O | -CH$_2$-(2,5-Cl$_2$-phenyl) |
| 38 | Q | $CH_3$ | O | -CH$_2$-(2,6-Cl$_2$-phenyl) |
| 39 | Q | $CH_3$ | O | -CH$_2$-(3,4-Cl$_2$-phenyl) |
| 40 | Q | $CH_3$ | O | -CH$_2$-(3,5-Cl$_2$-phenyl) |
| 41 | Q | $CH_3$ | O | -CH$_2$-(2,4,6-Cl$_3$-phenyl) |

TABLE 1-continued

Derivatives of 2-(1-Aryl-4-cyano-5-pyrazolylmethyleneiminooxy)-alkanoic Acids

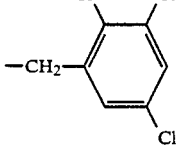

| Compound No | R | R¹ | Y | R² |
|---|---|---|---|---|
| 42 | Q | CH₃ | O | —CH₂— (2,4,5-trichlorophenyl) 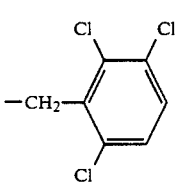 |
| 43 | Q | CH₃ | O | —CH₂— (2,3,6-trichlorophenyl) 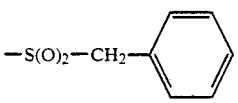 |
| 44 | Q | CH₃ | NH | —S(O)₂CH₃ |
| 45 | Q | CH₃ | NH | —S(O)₂-i-C₃H₇ |
| 46 | Q | CH₃ | NH | —S(O)₂—CH₂—phenyl 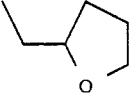 |
| 47 | Q | H | O | H |
| 48 | Q | H | O | CH₃ |
| 49 | Q | H | O | C₂H₅ |
| 50 | Q | H | O | i-C₃H₇ |
| 51 | Q | H | O | —CH₂SCH₃ |
| 52 | Q | H | O | —CH₂C≡CH |
| 53 | Q | H | O | —CH₂C≡CCH₂Cl |
| 54 | Q | H | O | tetrahydrofuranyl 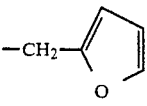 |
| 55 | Q | H | O | —CH₂-furyl 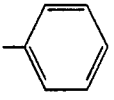 |
| 56 | Q | H | O | —phenyl |
| 57 | Q | H | O | —CH₂-phenyl 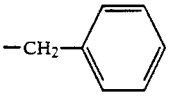 |
| 58 | Q | H | O | —CH₂-(3-chlorophenyl) 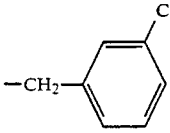 |
| 59 | Q | H | O | —N=C(CH₃)₂ |

TABLE 1-continued

Derivatives of 2-(1-Aryl-4-cyano-5-pyrazolylmethyleneiminooxy)-alkanoic Acids

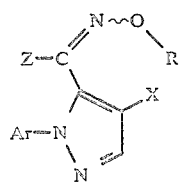

| Compound No | R | R¹ | Y | R² |
|---|---|---|---|---|
| 60 | CH₃ | — | — | — |
| 61 | (CH₂CH=CHCl) | — | — | — |
| 62 | Q | H | NH | CH₃ |
| 63 | Q | H | NH | —S(O)₂CH₃ |
| 64 | Q | H | — | —N(morpholinyl) |

When R = Q, Q = $\rangle$—C(O)—Y—R², Z = —OCH₃, and Ar = F₃C—(2,6-dichlorophenyl)

| 65 | Q | H | O | H |
| 66 Z isomer | Q | H | O | CH₃ |
| 67 E isomer | Q | H | O | CH₃ |
| 68 | Q | H | O | —CH₂SCH₃ |
| 69 | Q | H | O | —C₆H₄—NO₂ |

When R = Q, Q = $\rangle$—C(O)—Y—R², Z = H, and Ar = Cl—(2,6-dichlorophenyl)

| 70 | Q | CH₃ | O | H |
| 71 | Q | CH₃ | O | CH₃ |
| 72 | Q | CH₃ | O | —CH₂—C₆H₅ |
| 73 | Q | CH₃ | O | —CH₂CH₂CH₂Cl |

TABLE 2

Characterizing Properties

| Cmpd No. | mp (°C.) | Cmpd No. | mp (°C.) | Cmpd No. | mp (°C.) |
|---|---|---|---|---|---|
| 1 | 120–125 | 25 | 59–61 | 49 | semi-solid |
| 2 | oil | 26 | oil | 50 | 99–103 |
| 3 | 95–97.5 | 27 | oil | 51 | 117–120 |
| 4 | semi-solid | 28 | 74–75 | 52 | oil |
| 5 | oil | 29 | 86–88 | 53 | oil |
| 6 | 88–91 | 30 | 88–90 | 54 | 69–72 |
| 7 | oil | 31 | oil | 55 | oil |
| 8 | 70–74 | 32 | oil | 56 | oil |
| 9 | oil | 33 | oil | 57 | 65–68 |
| 10 | oil | 34 | oil | 58 | waxy solid |
| 11 | oil | 35 | oil | 59 | 103–106 |
| 12 | solid | 36 | oil | 60 | 98–100.5 |
| 13 | solid | 37 | resin | 61 | oil |
| 14 | 73–75 | 38 | 122–123 | 62 | 141–143.5 |
| 15 | 126–129 | 39 | oil | 63 | solid |
| 16 | solid | 40 | oil | 64 | oil |
| 17 | solid | 41 | oil | 65 | 160–163 |
| 18 | viscous oil | 42 | resin | 66 | oil |
| 19 | 136–142 | 43 | resin | 67 | 117–120 |
| 20 | 84–85 | 44 | 148–150 | 68 | 69–71 |
| 21 | oil | 45 | 146–149 | 69 | viscous oil |
| 22 | oil | 46 | solid | 70 | 107.5–110.5 |
| 23 | 115–120 | 47 | viscous oil | 71 | 111–113.5 |
| 24 | 77–79 | 48 | viscous oil | 72 | oil |
|  |  |  |  | 73 | oil |

TABLE 3

PREEMERGENCE HERBICIDAL ACTIVITY (% Control)

| Compound No. | 1 | 2 | 3 | 4 | 5 | 6 | 7 |
|---|---|---|---|---|---|---|---|
| Rate (kg/ha) | 0.1 | 0.1 | 0.1 | 0.1 | 0.1 | 0.1 | 0.1 |
| Species | | | | | | | |
| Soybean | 60* | 60 | 80 | 80 | 70* | 10 | 75 |
| Wheat | 75* | — | 80 | 75 | 75* | 10 | 85 |
| Corn | 100* | 75 | 90 | 95 | 90* | 50 | 100 |
| Velvetleaf | 100* | 100 | 100 | 100 | 100* | 80 | 100 |
| Morningglory | 100* | 100 | 100 | 100 | 100* | 75 | 100 |
| Chickweed | 90* | — | 100 | 100 | 100* | 75 | 90 |
| Cocklebur | 60* | 95 | 60 | 80 | 95* | 10 | 40 |
| Blackgrass | 90* | — | 95 | 95 | 95* | 20 | 80 |
| Green foxtail | 95* | 100 | 90 | 100 | 100* | 75 | 100 |
| Johnsongrass | 95* | 100 | 95 | 100 | 95* | 90 | 95 |

| Compound No. | 8 | 9 | 10 | 11 | 12 | 13 | 14 |
|---|---|---|---|---|---|---|---|
| Rate (kg/ha) | 0.1 | 0.1 | 0.1 | 0.1 | 0.1 | 0.1 | 0.1 |
| Species | | | | | | | |
| Soybean | 20 | 20 | 60 | 60 | 30 | 40 | 90 |
| Wheat | 80 | 75 | 80 | 80 | 60 | 75 | 90 |
| Corn | 100 | 90 | 95 | 80 | 90 | 90 | 85 |
| Velvetleaf | 100 | 100 | 100 | 100 | 100 | 100 | 100 |
| Morningglory | 100 | 100 | 100 | 100 | 100 | 100 | 100 |
| Chickweed | 90 | 80 | 95 | 100 | 80 | 100 | 85 |
| Cocklebur | 40 | 60 | 40 | 60 | 60 | 50 | 70 |
| Blackgrass | 75 | 95 | 75 | 95 | 70 | 90 | 95 |
| Green foxtail | 100 | 100 | 100 | 100 | 85 | 90 | 100 |
| Johnsongrass | 100 | 95 | 100 | 100 | 90 | 80 | 95 |

| Compound No. | 15 | 16 | 17 | 18 | 19 | 20 | 21 |
|---|---|---|---|---|---|---|---|
| Rate (kg/ha) | 0.1 | 0.1 | 0.125 | 0.1 | 0.1 | 0.1 | 0.1 |
| Species | | | | | | | |
| Soybean | 100 | 10 | 70 | 50 | 85 | 95 | 10 |
| Wheat | 100 | 15 | 80 | 85 | 95 | 80 | 10 |
| Corn | 100 | 85 | 100 | 100 | 100 | 90 | 30 |
| Velvetleaf | 100 | 100 | 100 | 100 | 100 | 100 | 80 |
| Morningglory | 100 | 100 | 100 | 100 | 100 | 100 | 100 |
| Chickweed | 100 | 100 | 70 | 85 | 15 | 100 | 80 |
| Cocklebur | 100 | 10 | 100 | 80 | 70 | 60 | 10 |
| Blackgrass | 95 | 10 | 60 | 20 | 15 | 100 | 60 |
| Green foxtail | 100 | 85 | 95 | 95 | 100 | 100 | 100 |
| Johnsongrass | 95 | 90 | 95 | 90 | 100 | 100 | 85 |

| Compound No. | 22 | 23 | 24 | 25 | 26 | 27 | 28 |
|---|---|---|---|---|---|---|---|
| Rate (kg/ha) | 0.1 | 0.1 | 0.1 | 0.1 | 0.1 | 0.1 | 0.1 |
| Species | | | | | | | |
| Soybean | 40 | 60 | 60 | 75 | 30 | 40 | 60 |
| Wheat | 60 | 75 | 30 | 60 | 10 | 20 | 70 |
| Corn | 90 | 70 | 70 | 30 | 0 | 70 | 40 |
| Velvetleaf | 100 | 100 | 100 | 100 | 100 | 100 | 100 |
| Morningglory | 100 | 100 | 100 | 95 | 100 | 100 | 100 |
| Chickweed | 100 | — | — | 90 | 100 | 90 | 80 |
| Cocklebur | 0 | — | — | 50 | 20 | 30 | 50 |
| Blackgrass | 80 | — | — | 75 | 90 | 60 | 80 |
| Green foxtail | 100 | 30 | 100 | 85 | 90 | 90 | 80 |
| Johnsongrass | 95 | 75 | 100 | 80 | 30 | 100 | 90 |

| Compound No. | 29 | 30 | 31 | 32 | 33 | 34 | 35 |
|---|---|---|---|---|---|---|---|
| Rate (kg/ha) | 0.1 | 0.1 | 0.1 | 0.1 | 0.1 | 0.1 | 0.1 |
| Species | | | | | | | |
| Soybean | 60* | 60* | 55* | 55* | 20 | 50 | 20 |
| Wheat | 35* | 25* | 10* | 20* | 30 | 0 | 0 |
| Corn | 35* | 5* | 20* | 20* | 20 | 30 | 0 |
| Velvetleaf | 100* | 100* | 100* | 100* | 100 | 100 | 100 |
| Morningglory | 100* | 95* | 100* | 100* | 95 | 75 | 95 |
| Chickweed | 100* | 95* | 100* | 100* | 100 | 80 | 90 |
| Cocklebur | 35* | 35* | 20* | 15* | 30 | 40 | 20 |
| Blackgrass | 70* | 70* | 75* | 40* | 40 | 30 | 50 |
| Green foxtail | 100* | 90* | 100* | 100* | 75 | 100 | 100 |
| Johnsongrass | 95* | 80* | 90* | 95* | 90 | 0 | 75 |

| Compound No. | 36 | 37 | 38 | 39 | 40 | 41 | 42 |
|---|---|---|---|---|---|---|---|
| Rate (kg/ha) | 0.1 | 0.1 | 0.1 | 0.1 | 0.1 | 0.1 | 0.1 |
| Species | | | | | | | |
| Soybean | 50 | 50 | 30 | 30 | 0 | 10 | 0 |
| Wheat | 20 | 30 | 0 | 10 | 0 | 0 | 0 |
| Corn | 0 | 10 | 0 | 40 | 10 | 0 | 0 |
| Velvetleaf | 100 | 100 | 100 | 100 | 100 | 100 | 100 |
| Morningglory | 100 | 100 | 100 | 100 | 100 | 80 | 80 |
| Chickweed | 100 | 100 | 100 | 100 | 100 | 100 | 90 |
| Cocklebur | 20 | 40 | 20 | 40 | 40 | 30 | 20 |
| Blackgrass | 75 | 80 | 75 | 70 | 40 | 70 | 40 |
| Green foxtail | 80 | 100 | 50 | 75 | 100 | 20 | 30 |
| Johnsongrass | 75 | 40 | 75 | 40 | 80 | 20 | 20 |

| Compound No. | 43 | 44 | 45 | 46 | 47 | 48 | 49 |
|---|---|---|---|---|---|---|---|
| Rate (kg/ha) | 0.1 | 0.1 | 0.1 | 0.1 | 0.1 | 0.1 | 0.1 |
| Species | | | | | | | |
| Soybean | 30 | 50 | 40 | 10 | 50 | 15 | 60 |
| Wheat | 0 | 50 | 10 | 0 | 0 | 10 | 20 |
| Corn | 0 | 40 | 50 | 0 | 5 | 5 | 30 |
| Velvetleaf | 100 | 100 | 100 | 100 | 100 | 100 | 100 |
| Morningglory | 100 | 100 | 100 | 100 | 100 | 100 | 100 |
| Chickweed | 100 | 100 | 100 | 90 | 90 | 100 | 10 |
| Cocklebur | 40 | 90 | 40 | 40 | 0 | 0 | 20 |
| Blackgrass | 50 | 85 | 30 | 80 | 70 | 40 | 20 |
| Green foxtail | 50 | 0 | 30 | 85 | 70 | 0 | 85 |
| Johnsongrass | 40 | 80 | 30 | 95 | 50 | 95 | 100 |

| Compound No. | 50 | 51 | 52 | 53 | 54 | 55 | 56 |
|---|---|---|---|---|---|---|---|
| Rate (kg/ha) | 0.1 | 0.1 | 0.1 | 0.1 | 0.1 | 0.1 | 0.1 |
| Species | | | | | | | |
| Soybean | 85 | 100 | 30 | 50 | 60 | 60 | 60 |
| Wheat | 40 | — | 0 | 20 | 10 | 40 | 50 |
| Corn | 30 | 10 | 0 | 20 | 20 | 60 | 75 |
| Velvetleaf | 100 | 100 | 95 | 100 | 95 | 100 | 100 |
| Morningglory | 100 | 90 | 100 | 100 | 100 | 100 | 100 |
| Chickweed | 100 | — | 70 | 100 | 10 | 60 | 75 |
| Cocklebur | 80 | 0 | 30 | 20 | 10 | 30 | 40 |
| Blackgrass | 80 | — | 50 | 30 | 0 | 70 | 95 |
| Green foxtail | 95 | 30 | 60 | 50 | 95 | 50 | 85 |
| Johnsongrass | 95 | 80 | 20 | 50 | 85 | 80 | 90 |

| Compound No. | 57 | 58 | 59 | 60 | 61 | 62 | 63 |
|---|---|---|---|---|---|---|---|
| Rate (kg/ha) | 0.1 | 0.1 | 0.1 | 0.1 | 0.1 | 0.1 | 0.1 |
| Species | | | | | | | |
| Soybean | 40 | 80 | 30 | 40 | 0 | 100 | 20 |
| Wheat | — | 30 | 10 | 10 | 0 | 50 | 0 |
| Corn | 10 | 80 | 30 | 75 | 0 | 90 | 0 |
| Velvetleaf | 100 | 100 | 100 | 100 | 30 | 100 | 100 |
| Morningglory | 100 | 100 | 100 | 95 | 30 | 100 | 100 |
| Chickweed | — | 95 | 100 | 100 | 85 | 70 | 95 |
| Cocklebur | — | 40 | 0 | 30 | 0 | 80 | 30 |
| Blackgrass | — | 80 | 90 | 75 | 10 | 20 | 60 |
| Green foxtail | 50 | 90 | 90 | 100 | 80 | 100 | 50 |
| Johnsongrass | 100 | 75 | 80 | 90 | 30 | 95 | 95 |

TABLE 3-continued

PREEMERGENCE HERBICIDAL ACTIVITY (% Control)

| Compound No. | 64 | 65 | 66 | 67 | 68 | 69 | 70 |
|---|---|---|---|---|---|---|---|
| Rate (kg/ha) | 0.1 | 0.1 | 0.1 | 0.1 | 0.1 | 0.1 | 0.1 |
| Species | | | | | | | |
| Soybean | 85 | 30 | 40 | 0 | 10 | 20 | 0 |
| Wheat | 75 | 20 | 20 | — | 10 | 10 | 0 |
| Corn | 80 | 10 | 60 | 10 | 0 | 0 | 0 |
| Velvetleaf | 100 | 85 | 30 | 85 | 95 | 60 | 100 |
| Morningglory | 100 | 30 | 40 | 10 | 10 | 30 | 70 |
| Chickweed | 90 | 0 | 10 | — | 0 | 0 | 60 |
| Cocklebur | 70 | 20 | 10 | — | 10 | 0 | 0 |
| Blackgrass | 70 | 30 | 10 | — | 0 | 0 | 20 |
| Green foxtail | 100 | 0 | 20 | 0 | — | 10 | 30 |
| Johnsongrass | 100 | 20 | 60 | 20 | 30 | 50 | 90 |

TABLE 3-continued

PREEMERGENCE HERBICIDAL ACTIVITY (% Control)

| Compound No. | 71 | 72 | 73 |
|---|---|---|---|
| Rate (kg/ha) | 0.1 | 0.1 | 0.1 |
| Species | | | |
| Soybean | 10 | 0 | 0 |
| Wheat | 10 | 10 | 0 |
| Corn | 20 | 0 | 0 |
| Velvetleaf | 100 | 100 | 80 |
| Morningglory | 70 | 70 | 20 |
| Chickweed | 60 | 5 | 20 |
| Cocklebur | 20 | 0 | 0 |
| Blackgrass | 0 | 0 | 0 |
| Green foxtail | 80 | 30 | 20 |
| Johnsongrass | 85 | 10 | 0 |

*average of two tests

TABLE 4

POSTEMERGENCE HERBICIDAL ACTIVITY (% Control)

| Compound No. | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| Rate (kg/ha) | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.125 | 0.1 |
| Species | | | | | | | | | | | | | | | | | | |
| Soybean | 90* | 90* | 90 | 95* | 85* | 60 | 90 | 85 | 90* | 95 | 95 | 90 | 90 | 90 | 95 | 85 | 95 | 90 |
| Wheat | 100* | 100* | 100 | 85* | 100* | 40 | 80 | 90 | 85* | 95 | 100 | 90 | 80 | 50 | 100 | 100 | 100 | 85 |
| Corn | 90* | 100* | 90 | 80* | 100* | 60 | 85 | 100 | 60* | 95 | 100 | 85 | 90 | 70 | 90 | 95 | 100 | 100 |
| Velvetleaf | 100* | 100* | 100 | 100* | 100* | 100 | 100 | 100 | 100* | 100 | 100 | 100 | 100 | 100 | 75 | 100 | 100 | 100 |
| Morningglory | 100* | 100* | 100 | 100* | 100* | 100 | 100 | 100 | 95* | 100 | 100 | 100 | 100 | 100 | 100 | 100 | 100 | 100 |
| Chickweed | 100* | 100* | 100 | 100* | 95* | 70 | 100 | 100 | 100* | 100 | 100 | 100 | 100 | 90 | 100 | 100 | 95 | — |
| Cocklebur | 100* | 100* | 100 | 100* | 100* | 75 | 100 | 95 | 100* | 100 | 100 | 100 | 100 | 85 | 100 | 100 | 100 | 80 |
| Blackgrass | 95* | 90* | 100 | 100* | 90* | 40 | 100 | 80 | 90* | 95 | 90 | 90 | 85 | 80 | 100 | 100 | 90 | 80 |
| Green foxtail | 100* | 100* | 100 | 100* | 100* | 100 | 100 | 100 | 100* | 100 | 100 | 100 | 100 | 100 | 100 | 100 | 95 | 85 |
| Johnsongrass | 95* | 100* | 100 | 100* | 100* | 90 | 95 | 100 | 100* | 100 | 100 | 100 | 95 | 85 | 100 | 100 | 90 | 95 |

| Compound No. | 19 | 20 | 21 | 22 | 23 | 24 | 25 | 26 | 27 | 28 | 29 | 30 | 31 | 32 | 33 | 34 | 35 | 36 |
|---|---|---|---|---|---|---|---|---|---|---|---|---|---|---|---|---|---|---|
| Rate (kg/ha) | 0.1 | 0.11 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| Species | | | | | | | | | | | | | | | | | | |
| Soybean | 90 | 85 | 85 | 80 | 80 | 90 | 90 | 90 | 85 | 90 | 90* | 85* | 90* | 85* | 75 | 70 | 75 | 80 |
| Wheat | 90 | 40 | 20 | 50 | 95 | 100 | 75 | 80 | 100 | 60 | 85* | 80* | 80* | 75* | 80 | 95 | 80 | 50 |
| Corn | 90 | 70 | 80 | 80 | 100 | 80 | 75 | 75 | 100 | 85 | 55* | 60* | 55* | 55* | 60 | 85 | 50 | 70 |
| Velvetleaf | 100 | 100 | 85 | 100 | 100 | 100 | 100 | 100 | 100 | 100 | 100* | 100* | 100* | 100* | 40 | 100 | 100 | 100 |
| Morningglory | 100 | 100 | 95 | 100 | 100 | 100 | 100 | 100 | 100 | 100 | 100* | 100* | 100* | 100* | 100 | 100 | 100 | 100 |
| Chickweed | — | 100 | 95 | 85 | 100 | 100 | 100 | 100 | 100 | 100 | 100* | 100* | 100* | 100* | 100 | 100 | 100 | 100 |
| Cocklebur | 70 | 80 | 40 | 80 | 100 | 100 | 85 | 100 | 100 | 100 | 100* | 100* | 90* | 100* | 100 | 60 | 100 | 100 |
| Blackgrass | 40 | 80 | 10 | 60 | — | — | 80 | 90 | 100 | 85 | 80* | 80* | 85* | 90* | 85 | 30 | 50 | 90 |
| Green foxtail | 100 | 100 | 60 | 95 | 100 | 100 | 95 | 95 | 100 | 100 | 100* | 100* | 100* | 100* | 85 | 100 | 100 | 100 |
| Johnsongrass | 95 | 75 | 75 | 90 | 100 | 100 | 100 | 100 | 100 | 90 | 95 | 100* | 95* | 95* | 100* | 90 | 100 | 80 |

| Compound No. | 37 | 38 | 39 | 40 | 41 | 42 | 43 | 44 | 45 | 46 | 47 | 48 | 49 | 50 | 51 | 52 | 53 | 54 |
|---|---|---|---|---|---|---|---|---|---|---|---|---|---|---|---|---|---|---|
| Rate (kg/ha) | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| Species | | | | | | | | | | | | | | | | | | |
| Soybean | 75 | 70 | 75 | 80 | 40 | 70 | 70 | 100 | 95 | 90 | 100 | 100 | 95 | 100 | 90* | 80 | 100 | 100 |
| Wheat | 50 | 60 | 60 | 75 | 50 | 60 | 40 | 95 | 75 | 20 | 85 | 80 | 90 | 90 | 90* | 80 | 70 | 95 |
| Corn | 50 | 75 | 75 | 80 | 70 | 60 | 60 | 90 | 100 | 90 | 95 | 90 | 70 | 80 | 95* | 50 | 60 | 75 |
| Velvetleaf | 100 | 100 | 100 | 100 | 100 | 100 | 100 | 80 | 100 | 85 | 90 | 100 | 100 | 100 | 100* | 100 | 100 | 100 |
| Morningglory | 100 | 75 | 100 | 100 | 100 | 100 | 75 | 100 | 100 | 100 | 100 | 100 | 100 | 100 | 100 | 100 | 100 | 100 |
| Chickweed | 100 | 100 | 100 | 100 | 100 | 100 | 100 | 100 | 100 | 95 | 85 | 100 | 95 | 90 | 100 | 100 | 90 | 100 |
| Cocklebur | 95 | 100 | 100 | 100 | 75 | 75 | 80 | 100 | 100 | 80 | 100 | 90 | 100 | 100* | 40 | 80 | 100 | |
| Blackgrass | 90 | 70 | 85 | 75 | 75 | 75 | 80 | 40 | 100 | 0 | 70 | 30 | 30 | 60 | 95 | 50 | 50 | 100 |
| Green foxtail | 100 | 100 | 100 | 100 | 100 | 95 | 85 | 100 | 95 | 90 | 30 | 60 | 30 | 80 | 85* | 50 | 50 | 100 |
| Johnsongrass | 100 | 95 | 100 | 100 | 95 | 90 | 80 | 85 | 100 | 75 | 90 | 90 | 90 | 90 | 100* | 85 | 90 | 95 |

| Compound No. | 55 | 56 | 57 | 58 | 59 | 60 | 61 | 62 | 63 | 64 | 65 | 66 | 67 | 68 | 69 | 70 | 71 | 72 | 73 |
|---|---|---|---|---|---|---|---|---|---|---|---|---|---|---|---|---|---|---|---|
| Rate (kg/ha) | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| Species | | | | | | | | | | | | | | | | | | | |
| Soybean | 95 | 95 | 90* | 100 | 90 | 80 | 70 | 90 | 95 | 90 | 50 | 40 | 40 | 40 | 80 | 80 | 75 | 85 | 30 |
| Wheat | 50 | 70 | 70* | 85 | 75 | 0 | 60 | 70 | 90 | 75 | 20 | 30 | 40 | 20 | 20 | 40 | 60 | 40 | 0 |
| Corn | 75 | 80 | 95* | 85 | 60 | 40 | 40 | 60 | 95 | 80 | 40 | 50 | 40 | — | 70 | 80 | 75 | 50 |  |
| Velvetleaf | 100 | 100 | 100* | 100 | 100 | 100 | 100 | 100 | 100 | 100 | 75 | 75 | 100 | 80 | 50 | 100 | 95 | 100 | 80 |
| Morningglory | 100 | 100 | 100* | 100 | 100 | 95 | 80 | 100 | 100 | 100 | 40 | 75 | 75 | 70 | 70 | 100 | 100 | 100 | 70 |
| Chickweed | 100 | 100 | 100 | — | 100 | 100 | 85 | 100 | 40 | 100 | 10 | 30 | — | 30 | 0 | 80 | 100 | 100 | 0 |
| Cocklebur | 100 | 95 | 100* | 100 | 100 | 70 | 30 | 60 | 100 | 95 | 20 | 50 | 40 | 60 | 30 | 80 | 80 | 50 | 0 |
| Blackgrass | 75 | 90 | 95 | 75 | 70 | 10 | 0 | 20 | 20 | 85 | 10 | 20 | — | 10 | 0 | 10 | 30 | 40 | 0 |
| Green foxtail | 50 | 80 | 70* | 90 | 90 | 60 | 85 | 90 | 50 | 90 | 40 | 95 | 0 | 20 | — | 100 | 80 | 85 | 0 |

TABLE 4-continued

| POSTEMERGENCE HERBICIDAL ACTIVITY (% Control) | | | | | | | | | | | | | | | | | | | |
|---|---|---|---|---|---|---|---|---|---|---|---|---|---|---|---|---|---|---|---|
| Johnsongrass | 90 | 100 | 95* | 100 | 90 | 20 | 80 | 100 | 95 | 100 | 50 | 70 | 10 | 70 | 85 | 80 | 60 | 90 | 0 |

*average of two tests

I claim:

1. A herbicidal compound of the formula

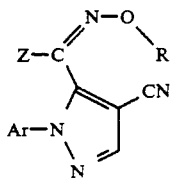

in which
R is lower alkyl, lower alkenyl, or lower alkynyl, each optionally substituted with halogen, or CH($R^1$)—C(O)—Y—$R^2$;
$R^1$ is hydrogen or lower alkyl;
$R^2$, when Y is O, is hydrogen, lower alkyl, lower alkenyl, lower alkynyl, lower haloalkyl, lower cyanoalkyl, phenyl, oxazolyl, isopropylideneimino, methylthiomethyl, furanylmethyl, tetrahydrofuranylmethyl, ammonium substituted with 1 to 3 lower alkyl, optionally substituted with halo or hydroxy, benzyl, optionally substituted with 1 to 3 halo or lower alkyl, and when Y is NH, is lower alkyl, lower alkylsulfonyl, or benzylsulfonyl;
Y is O or NH;
Z is hydrogen or lower alkoxy; and
Ar is 3-chloro-5-trifluoromethyl-2-pyridyl, 2-6-dichloro-4-trifluoromethylphenyl, or 2,4,6-trichlorophenyl.

2. A compound of claim 1 in which
R is CH($R^1$)—CO—Y—$R^2$;
$R^1$ is hydrogen or lower alkyl;
$R^2$, when Y is O, is hydrogen, lower alkyl, lower haloalkyl, lower cyanoalkyl, or benzyl, optionally substituted with 1-3 halo, and when Y is NH is lower alkyl, lower alkylsulfonyl, or benzylsulfonyl;
Z is hydrogen;
Ar is 3-chloro-5-trifluoromethyl-2-pyridyl or 2,6-dichloro-4-trifluoromethylphenyl; and
halo is chlorine or fluorine.

3. A compound of claim 2 in which $R^1$ is hydrogen or lower alkyl; and $R^2$, when Y is O, is hydrogen, lower alkyl, lower haloalkyl, or benzyl, optionally substituted with 1-3 halo, and when Y is NH is lower alkylsulfonyl.

4. A compound of claim 3 in which $R^1$ is methyl, and Ar is 3-chloro-5-trifluoromethyl-2-pyridyl.

5. The compound of claim 4 in which $R^2$ is methyl, and Y is O.

6. The compound of claim 4 in which $R^2$ is 3-chloropropyl, and Y is O.

7. The compound of claim 4 in which $R^2$ is methylsulfonyl, and Y is NH.

8. A compound of claim 3 in which Ar is 2,6-dichloro-4-trifluoromethylphenyl, and Y is O.

9. The compound of claim 8 in which $R^1$ and $R^2$ are each methyl.

10. The compound of claim 8 in which $R^1$ is methyl, and $R^2$ is 3-chlorobenzyl.

11. The compound of claim 8 in which $R^1$ is hydrogen and $R^2$ is isopropyl.

12. The compound of claim 8 in which $R^1$ and $R^2$ are each hydrogen.

13. A herbicidal composition containing a herbicidally effective amount of a compound of claim 1 in admixture with an agriculturally acceptable carrier.

14. A method of controlling undesired plant growth that comprises applying to the locus where the undesired plants are growing, or are expected to grow, a herbicidally effective amount of a composition of claim 13.

* * * * *